United States Patent
Musacchio et al.

[11] Patent Number: 5,897,758
[45] Date of Patent: Apr. 27, 1999

[54] SOLID CONTACT SYSTEM FOR POTENTIOMETRIC SENSORS

[75] Inventors: John Musacchio, Tyngsboro; Urs Oesch, Holliston, both of Mass.

[73] Assignee: Chiron Diagnostics Corporation, E. Walpole, Mass.

[21] Appl. No.: 08/904,744

[22] Filed: Aug. 1, 1997

Related U.S. Application Data

[63] Continuation of application No. 08/710,063, Sep. 10, 1996, abandoned, which is a continuation of application No. 08/312,486, Sep. 26, 1994, abandoned, which is a continuation of application No. 07/650,347, Feb. 4, 1991, abandoned.

[51] Int. Cl.$^6$ .................................................. G01N 27/333
[52] U.S. Cl. .......................... 204/418; 204/416; 257/253
[58] Field of Search ..................................... 204/416, 417, 204/418, 419; 257/253; 422/82.03

[56] References Cited

U.S. PATENT DOCUMENTS

| | | | |
|---|---|---|---|
| 4,361,473 | 11/1982 | Young et al. | 204/418 |
| 4,735,702 | 4/1988 | Reinhoudt et al. | 204/416 |
| 4,871,442 | 10/1989 | Yamaguchi et al. | 204/418 |

OTHER PUBLICATIONS

Karl Cammann, Working with Ion–Selective Electrodes, Springer–Verlag, Berlin, 1979 a month of publication not available, pp. 31–48.

Arthur K. Covington, editor, Ion–Selective Electrode Methodology, vol. 1, CRC Press, Inc., Boca Raton, Florida, USA, 1979 a month of publication not available, pp. 58–62.

*Primary Examiner*—Kathryn Gorgos
*Assistant Examiner*—William T. Leader
*Attorney, Agent, or Firm*—Arthur S. Morgenstern; Stanley Sacks; Robert P. Blackburn

[57] ABSTRACT

An improvement to the coated wire electrode has been accomplished via inclusion of a fortiophore into a sensor device. Sensor devices of the present invention include: an internal reference element; a membrane; and a fortiophore. Fortiophores are neutral charge carriers, which complex reversibly a corresponding ion of the conductive material used as the internal reference element. The fortiophore provides an electrochemically defined and reproducible solid internal contact between the membrane and the internal reference element. This solid internal contact, for example, in ion selective sensors, provides more reproducible potential offsets and better precision, and faster wet up. The fortiophores can be utilized in other electrochemical devices.

20 Claims, 17 Drawing Sheets

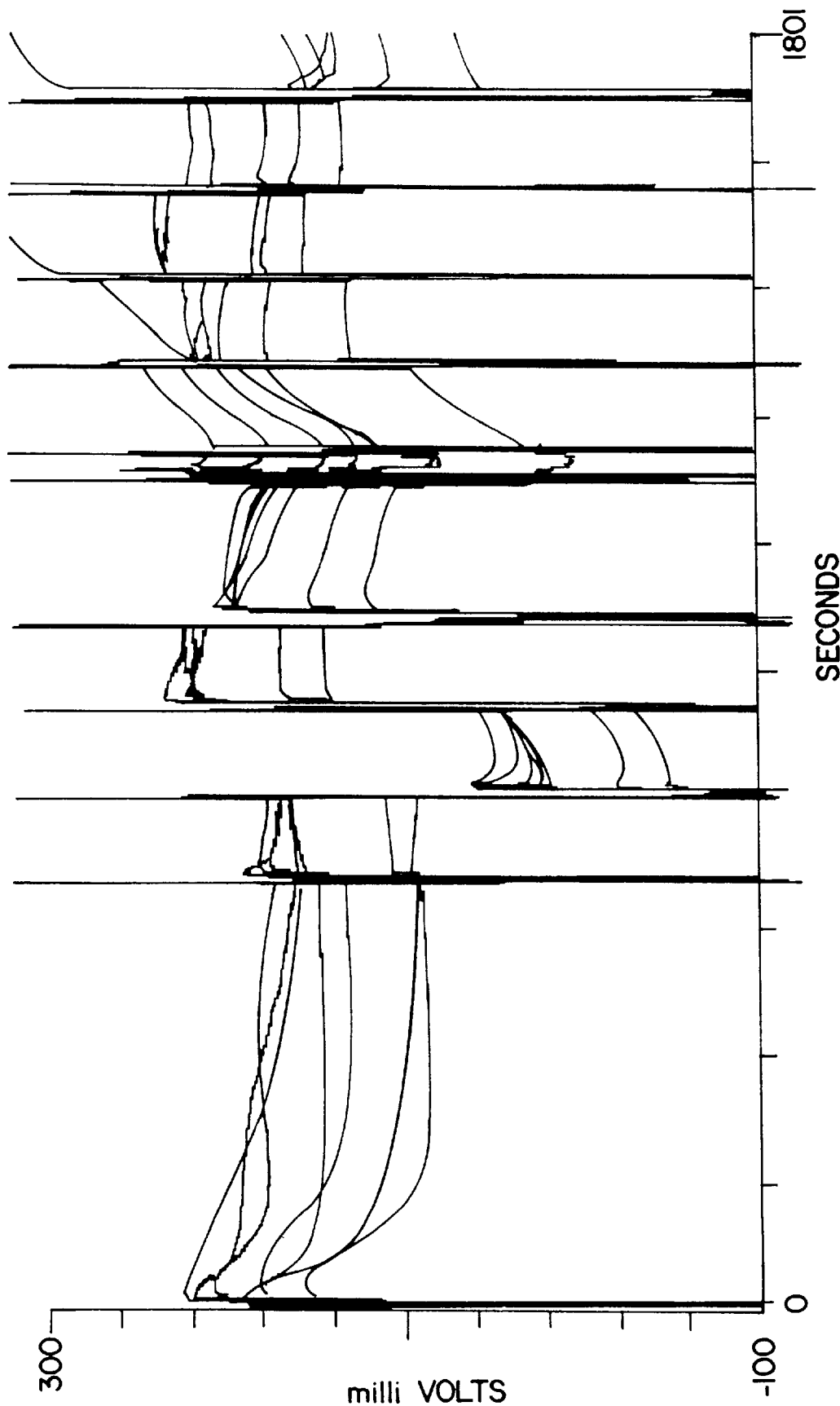

SOLID CONTACT SYSTEM FOR POTENTIOMETRIC SENSORS

This application is a continuation of application Ser. No. 08/710,063, filed Sep. 10, 1996, now abandoned, which is a continuation of application Ser. No. 08/312,486, filed Sep. 26, 1994, now abandoned, which is a continuation of application Ser. No. 07/650,347, filed on Feb. 4, 1991, now abandoned.

BACKGROUND OF THE INVENTION

1. Field of the Invention

The present invention relates to sensor devices, and more particularly, potentiometric sensors comprising an internal reference element, a membrane, and a fortiophore. The fortiophore, an electrochemical agent, interfaces the membrane and the internal reference element to form a solid internal contact.

2. Technical Review

Conventional sensors (3) known in the art (FIG. 1) have a layer of metal, e.g. Ag or other electrically conductive material, a layer of metal halide, e.g. AgCl, an aqueous or dry internal filling solution (usually containing the chloride salt of the cation being analyzed, e.g. KCl), and an ion selective membrane. See generally *Working with Ion-Selective Electrodes*, Camman, K. Springer-Verlag, 1979. The ion selective membrane includes an ionophore. See Ammann et al. *Helvetica ACTA* 1975, 58, 1535–1548. An ionophore is an ion-selective compound which is permselective, e.g. capable of complexing a desired ion and extracting it without a counterion into the interfacial zone of the membrane. The internal filling solution can form electrochemically defined interfaces with the metal halide on one side and the ionophore doped in the membrane. Such internal filling solutions actually contain a constant activity of the communicating ions which provide a high and dominating exchange current at both interfaces and therefore constant and predictable potentials at both the metal halide and the inner surface of the membrane. The outer surface of the membrane is exposed to the test sample. The potential generated at this interface is, according to the Nernst equation, dependant on the activity of the test sample ion, which the membrane is selective for.

Coated wire electrodes (CWE) have a layer of Ag or other conductive material, an optional layer of AgCl, and an ion selective membrane. See generally chapter four of *Principles of Chemical Sensors*, Janata, J., Plenum Press, 1989. There is no internal fill solution to interface the AgCl with the membrane to maintain the constant potential as in the conventional electrodes. The potential is therefore determined by unknown interfacial charge exchange agents or sites of uncontrolled activities. Potential measurements for the CWE tend to drift, have a slow response time, and have unreproducible potential offsets due to the undefined interface between the membrane and electrochemical internal reference element. In addition, any minute amounts of water soluable salt at the interface will cause water uptake causing drift in potential.

In attempting to reduce an ion selective sensor to a miniaturized planar configuration, problems arise due to differences in storage and measuring conditions. Water will permeate the membrane at any time to maintain osmotic balance. If water permeates from the sample into the internal electrolyte, the membrane will bulge or it may burst. If water leaves (e.g. evaporation) the sensor, the membrane will crenate. Moreover, this would change the activity of the internal electrolyte solution, thereby causing potential drift. This relationship is not considered in larger conventional electrodes because of the large reservoir of internal fill solution, but in a small sensor such as made by planar processing technologies, it becomes critical.

Shono et al., U.S. Pat. Nos. 4,554,362 and 4,523,994, describe the use of bis-crown-ether derivatives as neutral carriers in ion-selective membranes of ion-selective electrodes.

Delton et al., U.S. Pat. No. 4,504,368, describe the use of crown-ether compositions as ionophores in ion-selective compositions and electrodes. Various solvents are disclosed to solvate the crown ether and to provide ion mobility in the membrane.

Battaglia et al., U.S. Pat. No. 4,214,968, describe dry-operative ion selective electrodes incorporating the use of ionophores.

Freiser et al., U.S. Pat. No. 4,115,209 describe an electrode formed by coating a conductive substrate with an ion exchange material in a matrix. A listing of potentiometrically measurable ion or group of ions is provided.

Baginski et al., EP 0 267 724, disclose a method of printing an electrochemically active material on a substrate to provide a test device for carrying out a microchemical test.

Oue et al., *Chem. Ltr.* 1988, 409–410 disclose the use of monothiacrown ether (MTCE) as a neutral carrier for Ag-selective electrodes. It is noted that Que in a letter dated Sep. 6, 1988 recommended that if the compound is used as a neutral silver ion carrier, it should be first complexed with $AgNO_3$ in order to reduce conditioning time.

Daunert et al., *Anal. Chem.* 1990, 62, 1428–1431 describe ion-selective electrodes including an ionophore covalently attached to a polymeric matrix.

Oue, M. et al., *J. Chem. Soc.-Perkin Trans.* 1989, 1675–1678 disclose the use of lipophilic mono-and di-thiacrown ethers as neutral carriers of polymeric membrane $Ag^+$-selective electrodes.

SUMMARY OF THE INVENTION

In general, the present invention is directed to a sensor device formed of an internal reference element having an electrically conductive substrate; a membrane; and a fortiophore. A controlled solid electrochemical interface between the membrane and the internal reference element is maintained by the fortiophore. The fortiophore forms a complex with the conductive ion, e.g. metal, of the electrically conductive substrate which provides a true and reproducible electrical solid internal contact between the membrane and the electrically conductive substrate. The membrane includes an ionophore which forms a complex with an ion in a test sample and forms the electrochemical interface of the membrane with the test sample. The sensor device may be constructed in various forms, e.g. planar, coated wire, ISFET; which depending on the form chosen may require a base component. In one embodiment a planar sensor is formed of an internal reference element printed on a base of suitable non-conductive material with a membrane disposed over the internal reference element and a fortiophore.

In contrast to a neutral ionophore, the fortiophore is a neutral complexing agent which does, but does not need, to be ion-selective. Its only purpose is to provide a reversable electrochemical communication with the internal reference element and the membrane. It does not interface with the electrochemical action of the ionophore at the sample/membrane interface.

The use of a fortiophore allows for the elimination of two layers, the metal halide and the liquid or dry internal fill, from the conventional sensor configuration (FIG. 1). The resulting sensor of the present invention (FIG. 2) comprises a two layer system, which is easier to manufacture. Another advantage is that the sensor is not water susceptible due to the absence of an internal electrolyte fill.

It is noted that the terms sensor and chip in the specification and claims are used interchangeably.

It is to be understood that the representations in the FIGS. 1–5 are diagrammatic and that no attempt has been made to indicate actual scales or ratios.

Accordingly, it is a primary object of the present invention to provide a two layer sensor device having an internal reference element and a membrane, which are electrochemically interfaced by a fortiophore.

It is another object of the invention to provide an ion selective sensor comprising an internal reference element, an ion selective membrane, and a fortiophore; the membrane including an ionophore. The fortiophore forms a complex with the metal ion of the internal reference element and therefore provides a solid internal contact between the internal reference element and the membrane to interface the membrane with the internal reference element. The ionophore forms a complex with an ion which may be an anion or a cation in a test sample to interface the membrane with the test sample.

A still further object of the invention is to provide ion selective sensors which have more reproducible standard potentials, better precision and faster wet up.

It is a still further object of the invention to provide a planar potentiometric sensor.

It is another object of the invention to provide a coated wire sensor.

Another object of the invention is to provide a reproducible solid state contact for ISFET sensor.

Still another object of the present invention is to provide a sensor design to facilitate mass manufacturing of sensors which exhibit sensor to sensor reproducibility and a long shelf life.

A further object of the invention is to provide a sensor device including a fortiophore and at least one ionophore.

With these and other objectives in view, as will be apparent to those skilled in the art, the invention resides in the combination of materials set forth in the specification and covered by the claims appended hereto.

ABBREVIATIONS

The following abbreviations are used in the specification, accompanying tables and claims:
THF Tetrahydrofuran
VAL Valinomycin
PVC Poly (vinylchloride)
KTPB Potassium tetraphenyl borate
TOTM Trioctyl trimellitate
UDCN Undecyl cyanide
DTCE 1,10-Dithia-18-crown-6-ether
MTCE Dodecyl-16-crown-5-ether
AgTpClPB Silver tetrakis (p-chlorophenyl) borate
BHTCH Tetra-n-hexyl-3,3',4,4'-benzhydrotetracarboxylate
ONPOE o-nitrophenol octyl ether
SHONO Bis (12-crown-4) methyldodecyl malonate
TDDA Tridodecylamine
ETH 1001 (−)-(R,R)-N,N'-[BIS(11l-ethoxycarbonyl) undecyl]-N,N'-4,5-tetramethyl-3,6-dioxaoctane diamide
KTpClPB Potassium tetrakis (p-chlorophenyl) borate
AgBENZ Silver Benzoate
DUP Diundecyl phthalate
ETH 2120 N,N,N',N'-Tetracyclohexyl-1,2-phenylenedioxydiacetamide
IFSET Ion-sensitive field effect transistors

BRIEF DESCRIPTION OF THE DRAWINGS

FIG. 20 is a graph showing wet up results for chip 129-34-6 for potassium measurement.

DESCRIPTION OF THE PREFERRED EMBODIMENT

Figure 1:
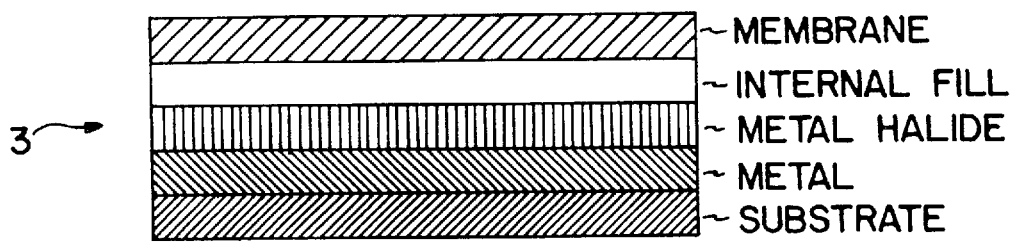
FIG. 1 is a sectional schematic view of a conventional electrode device.
Figure 2:
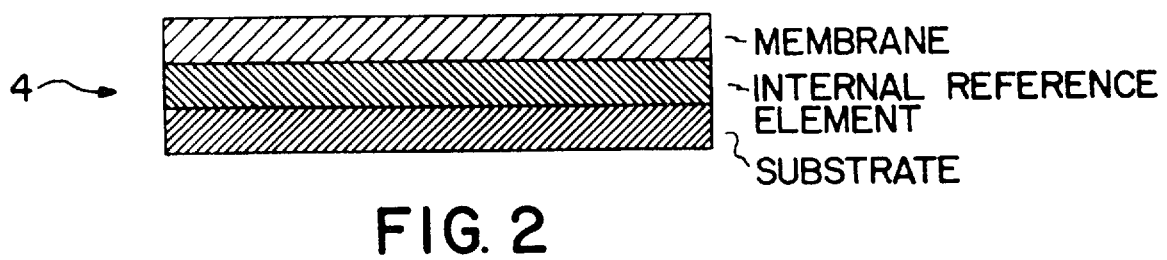
FIG. 2 is a sectional schematic view of a potentiometric device constructed in accordance with the present invention.

Referring to FIG. 2 sensor device (4) of the present invention includes a base component (10) which is comprised of an inert substrate; an internal reference element (12); and a membrane (20). There are many factors to be considered in selecting an inert substrate as generally described in chapter 4 of the *Handbook of Thick Film Hybrid Microelectronics*, C. A. Harper, McGraw-Hill Book Company, Reissue, 1982.

Figure 4:
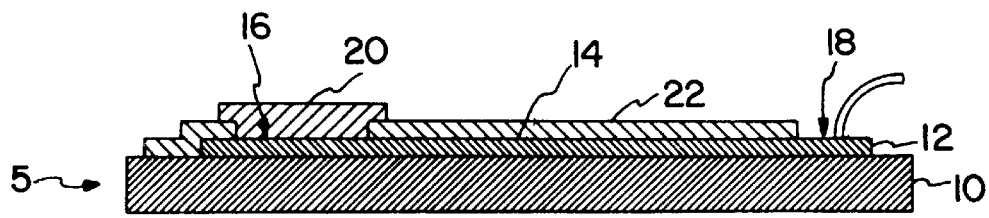
FIG. 4 is a sectional schematic view of a planar type sensor constructed in accordance with the present invention.

One configuration of the substrate (10) for the sensor device is a plane. The preferred composition of the substrate in the planar sensor device, FIG. 4, is alumina. The size of the plane will vary in accordance with the number of internal reference elements deposited onto the substrate, the design requirements attendant for various applications of the chip and the manufacturing considerations of producing the chips. The internal reference element (12) of the preferred embodiment are electrically conductive substrates, e.g. metals, alloys or a non-metal and metal or alloy mixture, etc.

Figure 3:
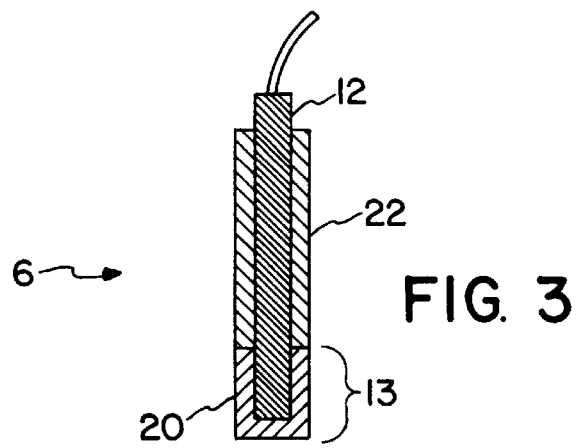
FIG. 3 is a sectional schematic view of a coated wire type sensor constructed in accordance with the present invention.

Alternatively, another embodiment of the CWE type (6) of the sensor device comprising a wire (12) with exposed tip (13) shown in FIG. 3; with the membrane (20) being deposited on the exposed tip of the wire.

Figure 5:
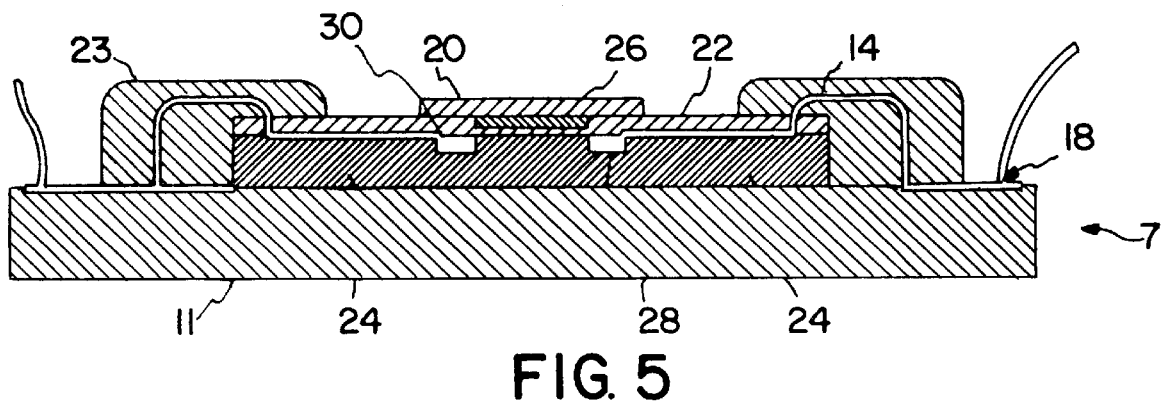
FIG. 5 is a sectional schematic view of a ISFET type sensor constructed in accordance with the present invention.

A sensor device integrated with microelectronic elements, e.g. ISFET (7) is shown in FIG. 5. The ISFET mounted on a base component (11) includes a silicon substrate (24); a conductive material gate (26); a drain (28); a source (30); an insulator (22), an encapsulation zone (23); and a membrane (20). See generally *Ion Selective Electrodes in Analytical Chemistry*, Vol. 2, Freiser, H., Plenum Press, New York, 1979.

Referring to FIG. 4, one or more electrically conductive leads (14) are deposited on the substrate; each of the conductive leads including a sensor site (16) and a contact area (18). The contact area provides means for being connected to a measuring device. The conductive lead is ordinarily comprised of a metal and an optional binder. The metal may consist of noble metals such as silver, platinum, gold, palladium, iridium or alloys thereof, the choice of which depends on the performance characteristics sought for a particular application of the sensor. Alternatively, the conductive substrate includes a mixture of a non-metal substance(s) and a metal or alloy. In the chips described below, silver is the preferred electrically conductive lead, unless otherwise stated.

An insulating material (22) is applied over a portion of the electrically conductive lead, see FIGS. 3–5. The insulating material is applied preferentially over a portion of the conductive lead to separate sensor site from the contact area.

The insulating material in the planar sensor is a dielectric material. Other types of insulating materials are well known in the art; the use of which would depend on the type and manufacturing requirements of the sensor device.

In the planar sensor embodiment of the present invention, a selected conductive lead as well as the insulating layer between the contact area and sensor site are printed onto the chip by conventional screening and firing techniques. If the sensor device is an ion-selective sensor then the membrane that is applied to the sensor site is an ion-selective membrane. An ionophore is a component of the membrane of the sensor device. The choice of ionophore will depend in part on the desired ion that is to be analyzed by the sensor device.

The printed chips may be optionally cleaned prior to the application of the membrane. One manner of cleaning is as follows: The chips are placed in a beaker containing 2-Propanol. The beaker is then placed in a heated, water-filled ultrasonic cleaner and sonicated for approximately 15 minutes. Next, the chips are removed from the beaker and rinsed with distilled water. The conductive substrate of the chips are washed with a 1M $HNO_3$ solution for 30 seconds, then rinsed with distilled water and dried in an oven at 100° C. for 1.5 hours. Other means of cleaning the chips may be utilized and are known by those skilled in the art.

In some of the sensors, as noted below, the conductive substrate was chloridized prior to the application of the ion selective membrane (see Table 1 membrane cast on Ag/AgCl). A 0.08% solution of $FeCl_3$ was applied to the chips for up to 2 minutes, then rinsed with distilled water and blotted dry.

In one sensor device of the present invention, planar potassium sensor 2-39-10, the ion selective membrane (See Table 1) was cast on blank silver electrodes on the chip. The membrane materials were first weighed into a glass vial, and 4.0 ml of THF was added. The resulting slurry was stirred until all the PVC dissolved. Then 0.01 g. of silver salts was added and the solution stirred for an additional 1.5 hours. The solution was then filtered using a 2 micron filter (Millipore). Next, eighteen drops of the resulting membrane solution were then cast onto the chip and the THF was evaporated under controlled conditions, rendering a cured membrane of about 50 micron thickness.

Alternatively, instead of adding $AgNO_3$ (as the appropriate metal salt) the chip is soaked for 12 h in 100 mM silver nitrate solution.

The fortiophore gives the electrodes good reproducibility sd=1.72 mV for one chip, and 1.96 mV is the average of two chips, and 2.10 mV is the standard deviation across the two chips. The selectivity over sodium, calcium and pH are shown to be within acceptable limits (see Table 3). Wet up is fast (see FIG. 6), and using a calculated differential measurement (take the difference of each individual electrode with the average of the four electrodes on a chip), the wet up is very fast (see FIG. 7).

In order to compare the two layer sensors of the present invention having an ion selective membrane including a fortiophore and without a fortiophore, a wet up of eight chips (four electrodes/chip) with and without fortiophore and membranes with and without KTPB was done (Table 1 membranes, and FIGS. 6, and 8–10). Table 2 shows the standard deviation of the four electrodes on a chip, 60 seconds post immersion, for the eight different conditions (note that the data with fortiophore as the average of two chips, while the data without fortiophore is one chip). The data shows three important points: the offset potential reproductivity is better with fortiophore present (if one omits the 33.9); membranes cast on Ag rather than AgCl perform better; and membranes without KTPB perform slightly better (with regard to offset potential reproducibility).

Figure 6:
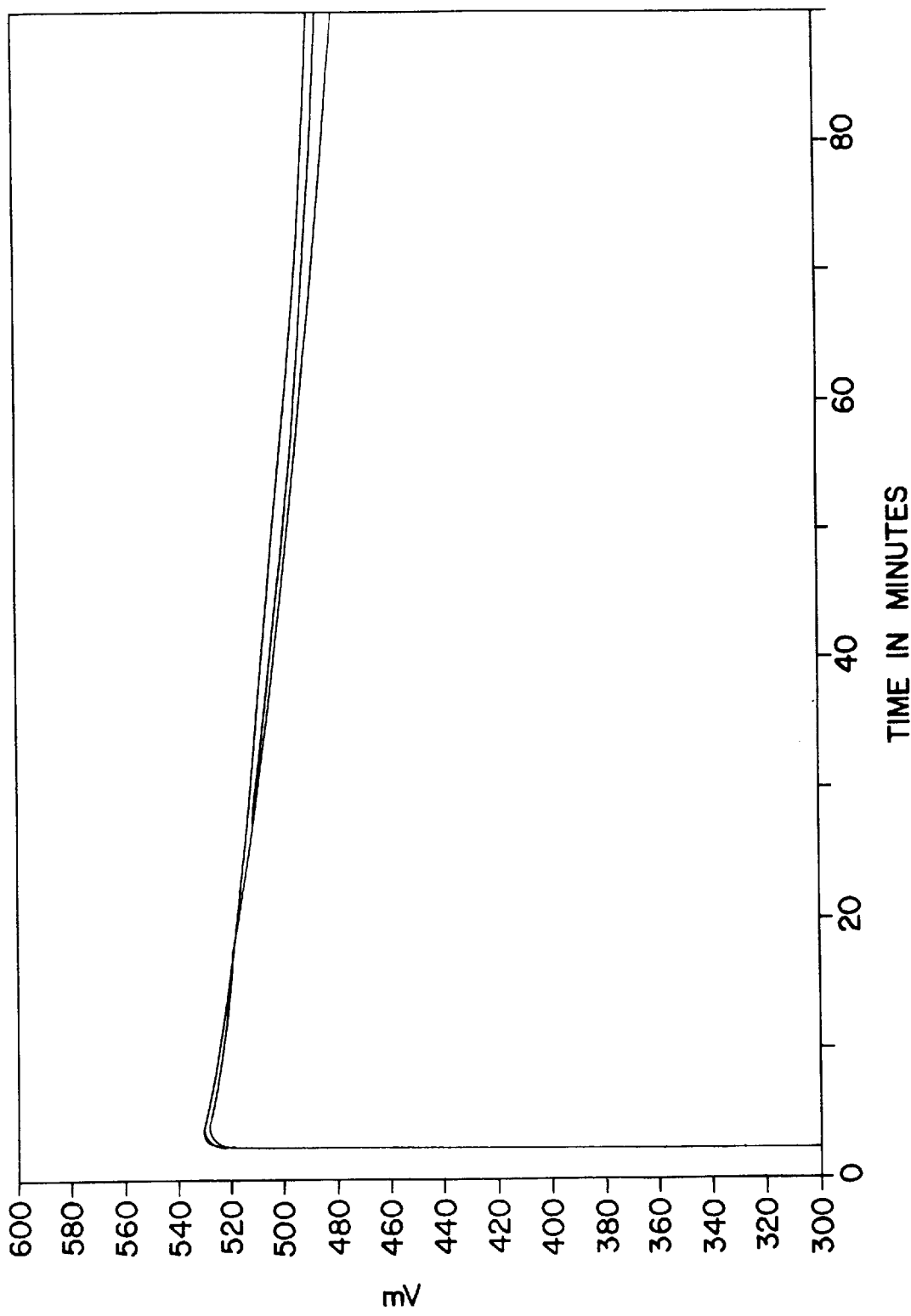
FIG. 6 is a graph showing wet up results for chip 2-6-1.
Figure 7:
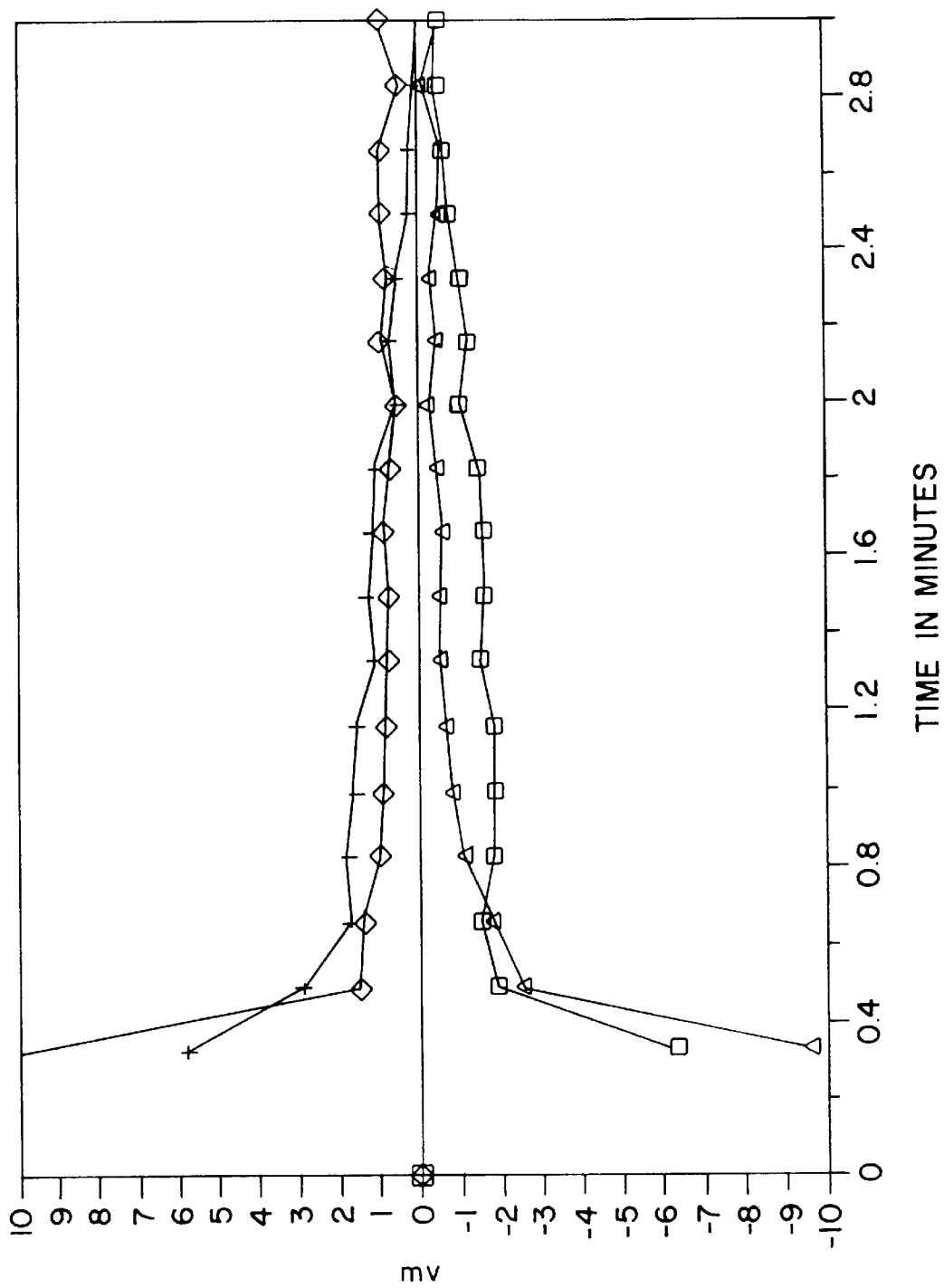
FIG. 7 is a graph showing differential measurement results for chip 2-6-1.
Figure 8:
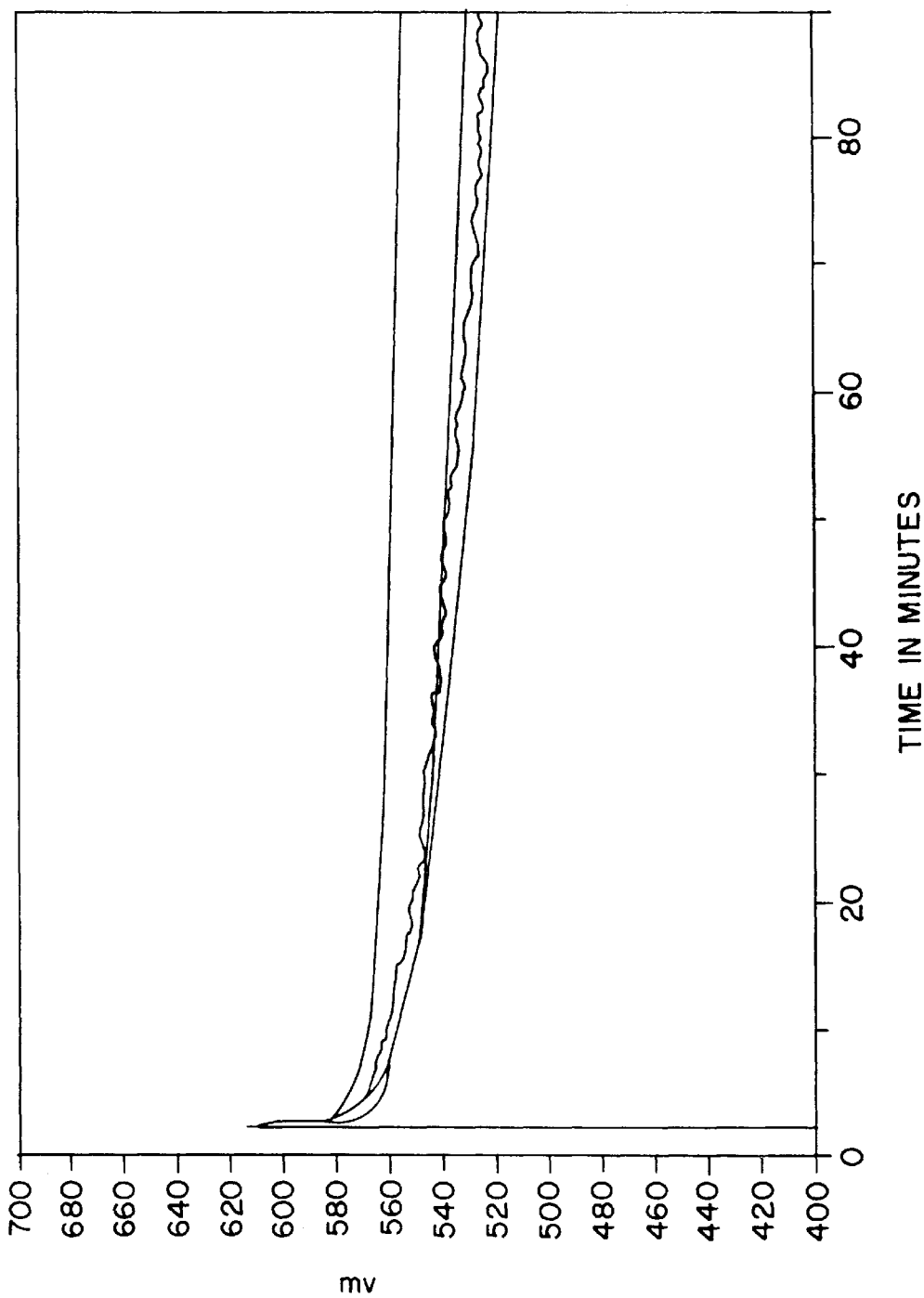
FIG. 8 is a graph showing wet up results for chip 2-19-1.
Figure 9:
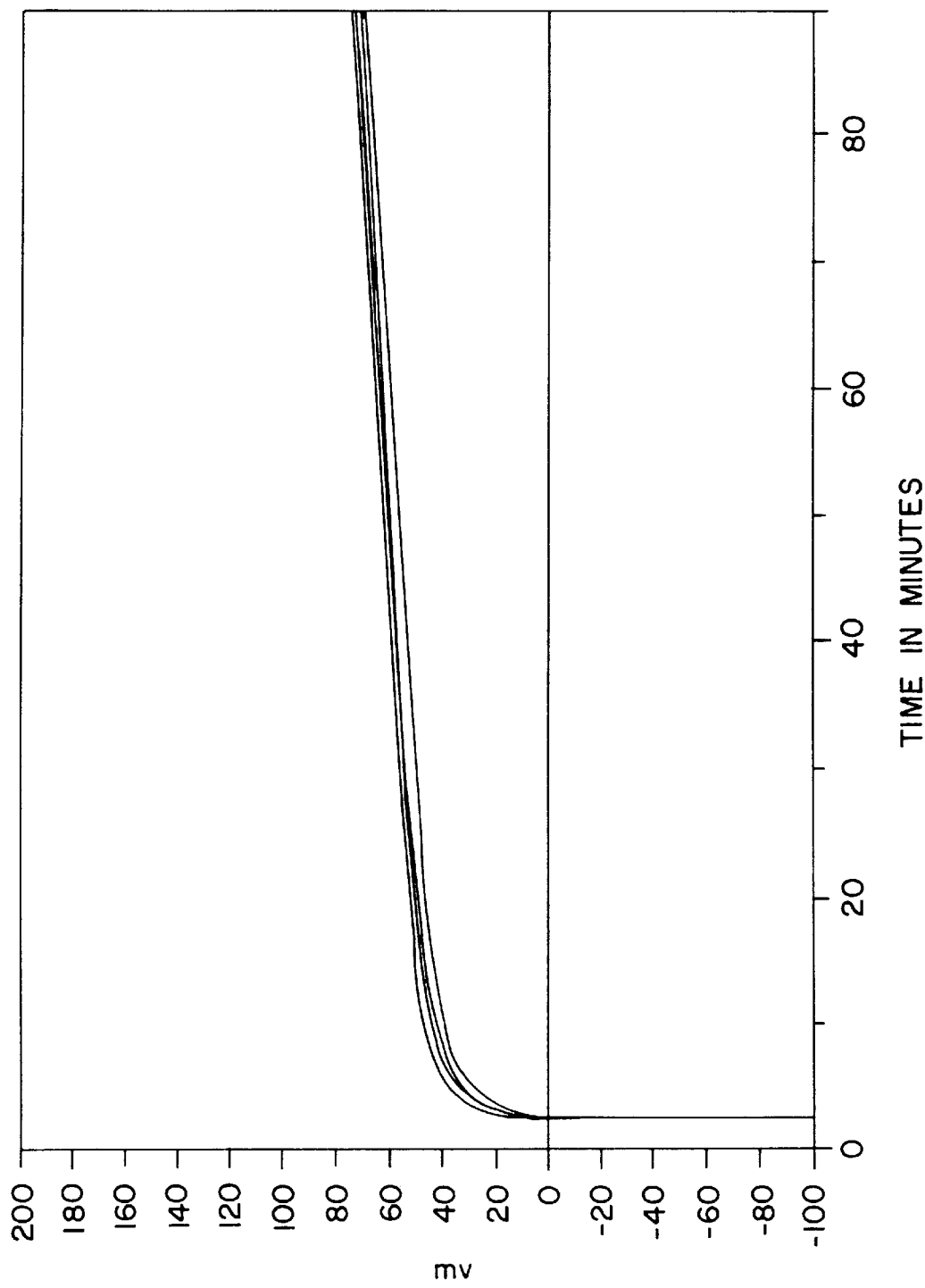
FIG. 9 is a graph showing wet up results for chip 2-6-7.
Figure 10:
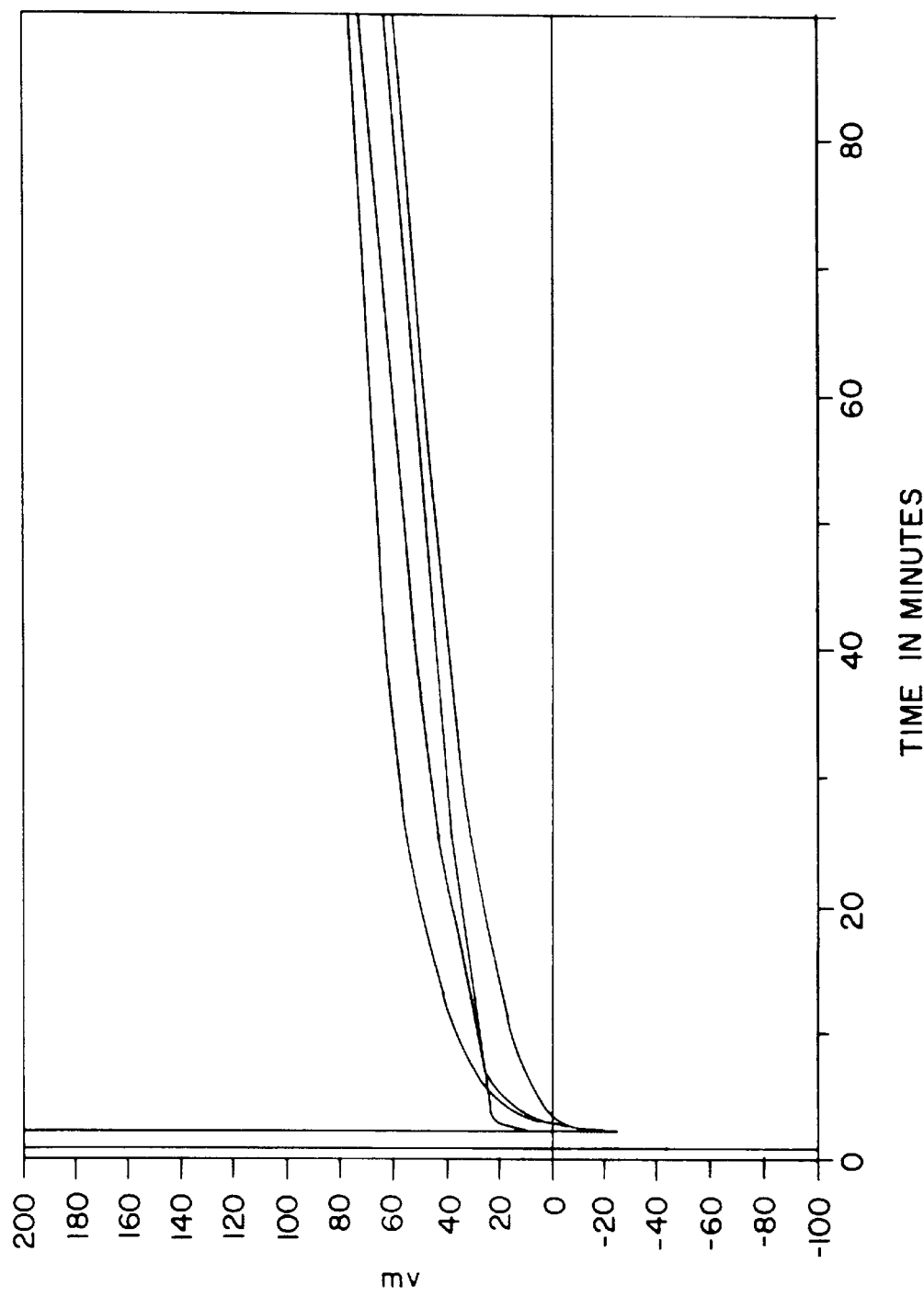
FIG. 10 is a graph showing wet up results for chip 2-19-4.
Figure 11:
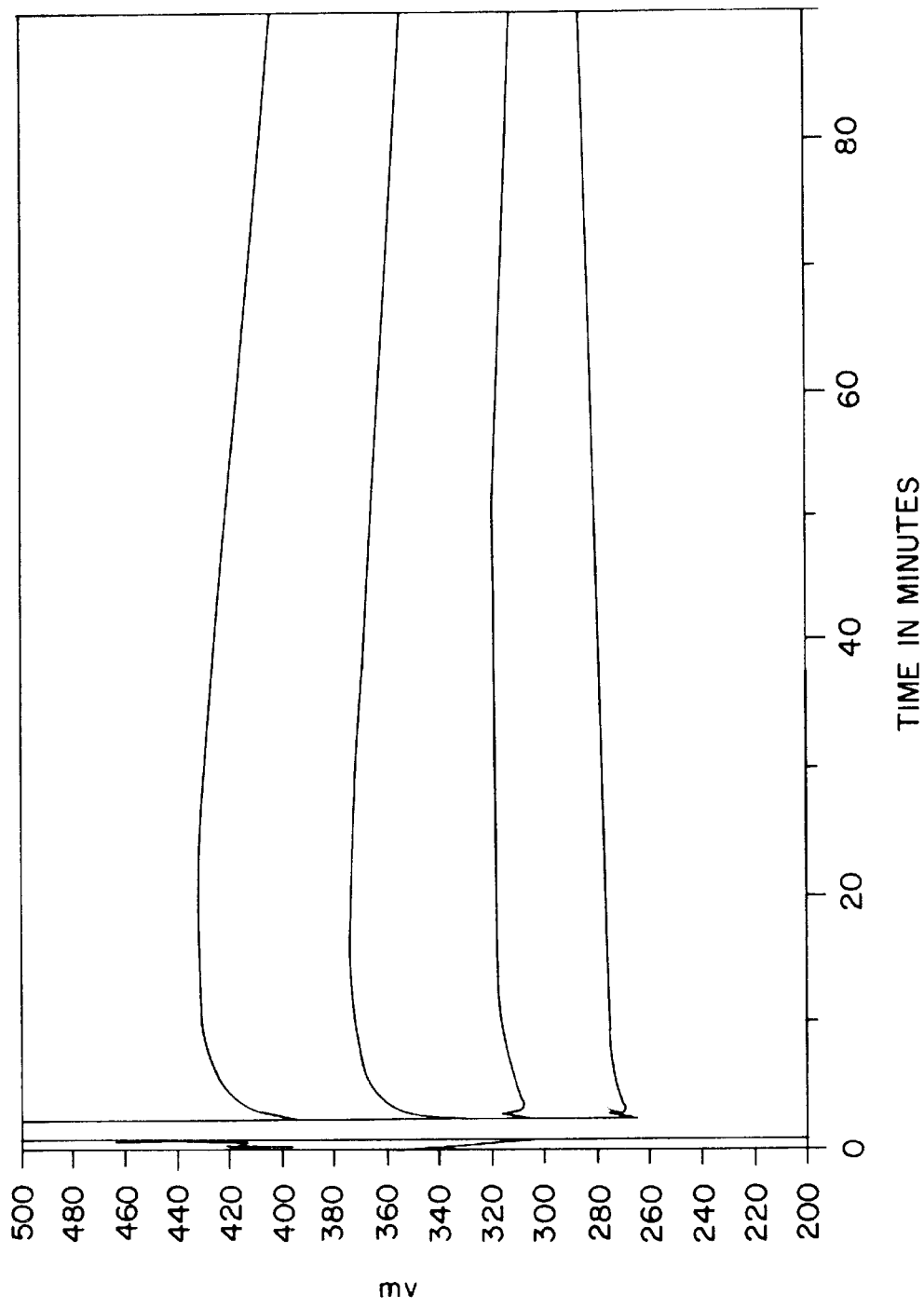
FIG. 11 is a graph showing wet up results for chip 2-39-10 in response to potassium.
Figure 12:
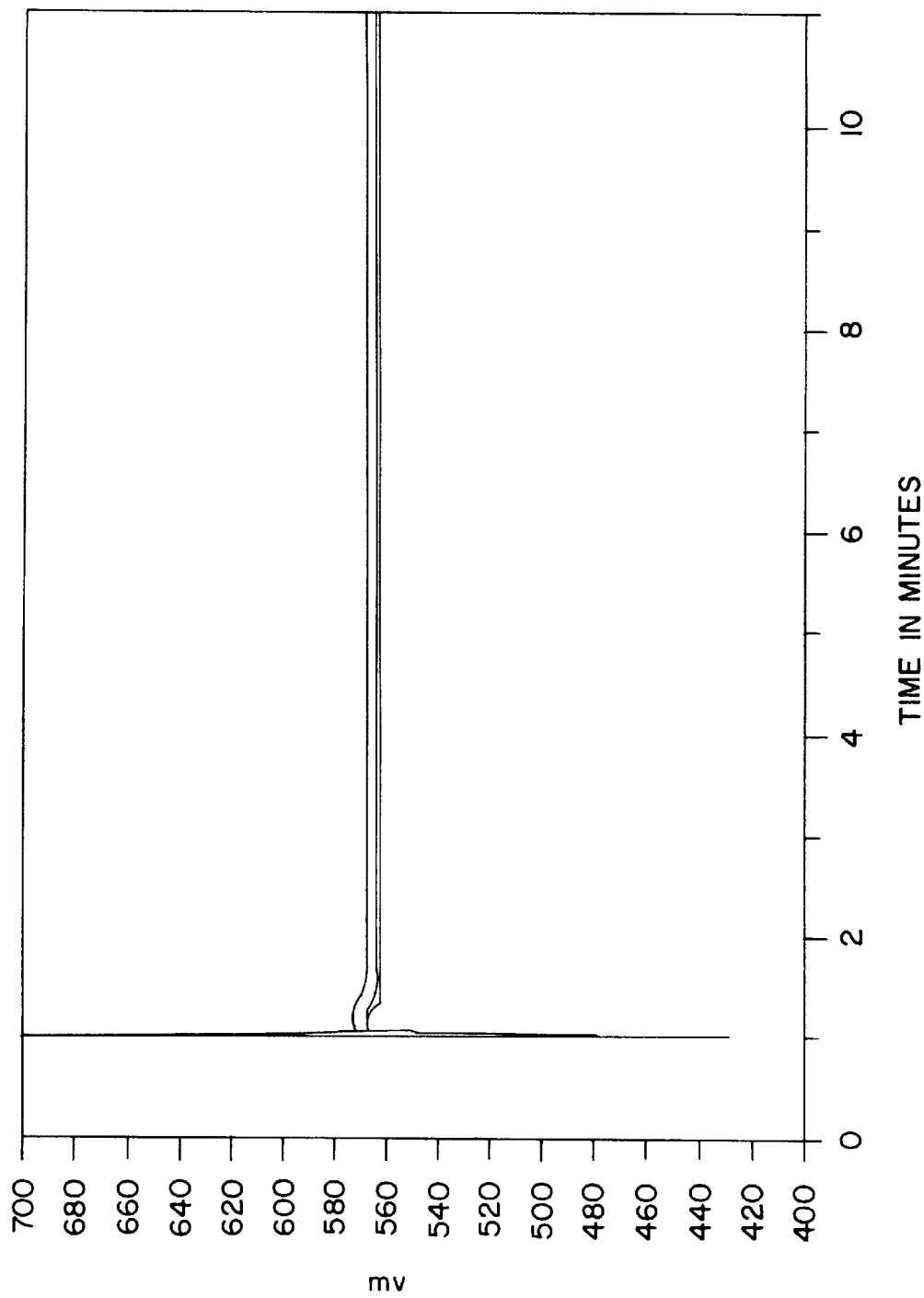
FIG. 12 is a graph showing wet up results for chip 2-180-3 in response to potassium.
Figure 13:
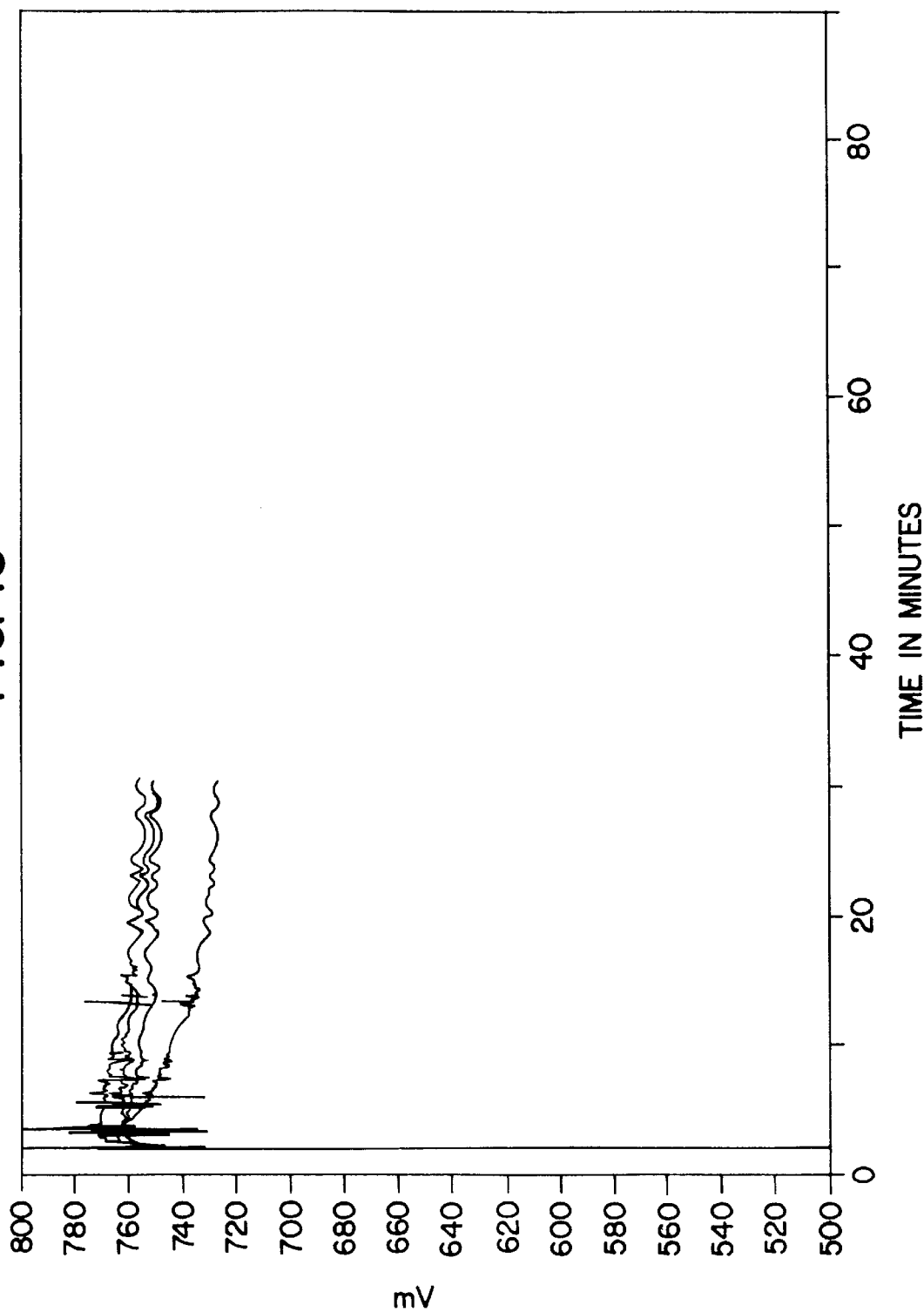
FIG. 13 is a graph showing wet up results for chip 2-53-10.
Figure 14:
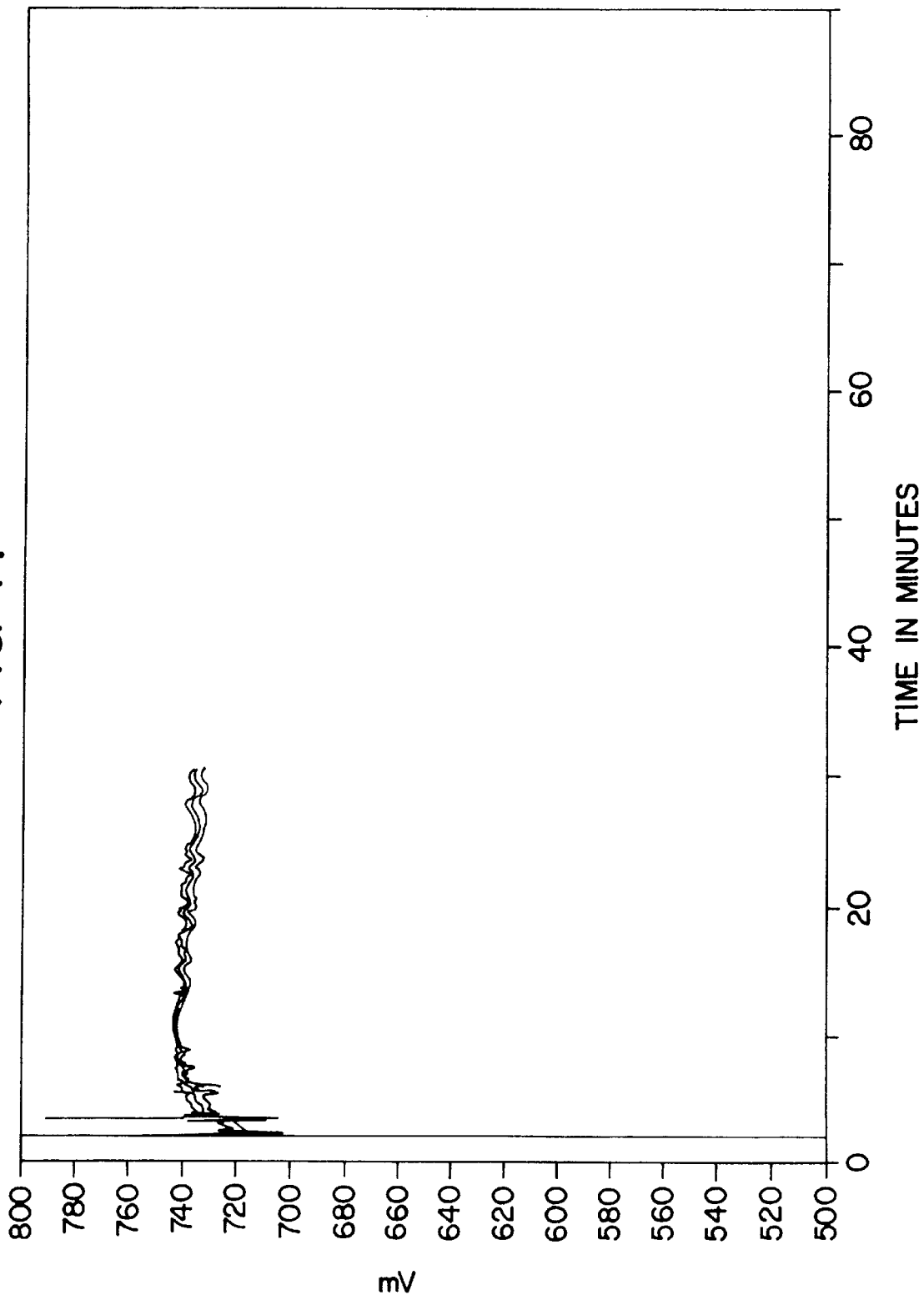
FIG. 14 is a graph showing wet up results for chip 2-53-9.

Chips 2-6-1 and 2-6-7 demonstrate good offset potential reproducibility (sds of 1.72 and 3.57), and good wet ups results (FIGS. 6 and 9). FIG. 7 shows the differential measurement results of chip 2-6-1 (the average of four electrodes minus an individual) for the first three minutes after the sensor was immersed in a 10 mmolar KCl solution.

Table 3 summarizes the selectivity and slope data. Both sensors meet the requirements for selective measurement of potassium in a physiological background. The slopes are comparable to the theoretically calculated slopes.

Table 4 summarizes some precision data taken by measuring some "mock" cals, ten aqueous "samples", and then two more "mock" cals. The precision numbers are calculated at 10, 30, 44, and 90 seconds after the sensors were immersed in the sample or cal. The first two rows of data are the average standard deviation of (four electrodes on a chip vs. a Corning double junction reference electrode) ten measurements in the same solution. No data was within the 0.53 mV spec for sample precision. The next two rows of data are the average standard deviation of (four electrodes on a chip) differentially measuring the same solution ten times. Note that the precision here is significantly better than versus a reference electrode, and meets the specification at 30 seconds post immersion. The last two rows of data are also differential measurements, but across both cals and samples. Note that because this was a differential measurement, the offset potential readings should be the same and the standard deviation results should also be low. Here the precision is better than versus a reference electrode, but not in the specification.

The preferred membrane formulation for the potassium sensor, see Table 9, uses MTCE as the fortiophore, AgBENZ as the silver salt, DUP as the plasticizer, PVC as the support, and VAL as the ionophore. This membrane, as compared to the membrane without MTCE, has significantly lower standard deviation of the absolute potentials, and lower drift (at 60 seconds) due to a faster wet up (see Table 1 and FIGS. 17–20).

Similar results have also been observed for sensors incorporating variations in weight percentages of membrane components. Particular attention has been given to varying the amount of metal salt, e.g. Ag salt in the membrane. It is apparent that while the amount described is optimal, a smaller or larger amount (0.5 times to 2 times the amount) still improves the results compared to no Ag salt or MTCE. Different classes of silver salts have been tried such as borates, e.g. silver tetraphenyl borate, silver tetrakis p-chlorophenyl borate, silver salycilate; organic carboxylates, e.g. silver benzoate; and organic sulfonates.

Different plasticizers have been tried including: phthalates, sebacates, ETH 2112, and tetra-n-hexyl-3,3',4,4'-benzhydrol tetracarboxylate. All showed similar results, with more lipophilic ones showing a faster response. The plasticizers are utilized with the polymer material to obtain a more homogeneous membrane with increased internal mobility. Plasticizers other than those noted above may serve the same purpose.

It is anticipated that the use of other suitable fortiophores, e.g. neutral complexing agents, may serve the same purpose and may be utilized in accordance with the present invention. The fortiophore may be disposed on the membrane, or dispersed in the membrane, or disposed between the internal reference element and the membrane, or immobilized on said internal.

In contrast to a neutral ionophore, the fortiophore is a neutral complexing agent which does, but does not need, to be ion-selective. Its only purpose is to provide a reversible electrochemical communication with the internal reference element and the membrane. It does not interface with the electrochemical action of the ionophore at the sample/membrane interface.

The use of a fortiophore allows, for example, the elimination of the liquid or dry internal fill, from the conventional sensor configuration. The resulting sensor is easier to manufacture, performs well, and has a long shelf life. Another advantage is that the sensor is not water susceptible due to the absence of an internal electrolyte fill. UDCN and DTCE are examples of other fortiophores, which are complexing agents for Ag ions and function in the same manner of DTCE of the preferred embodiment with Ag as the internal reference element. See Table 5. Table 5 provides a summary of potassium sensor data with various fortiophores. In all cases, the standard deviation of their offset potentials is significantly smaller than that observed for membranes without any fortiophore.

PVC is the preferred support material; however, any film forming polymeric material or any material which is capable of being polymerized into a film forming material, or any material which is cross-linkable into a polymeric film may be used as a support.

Figure 15:
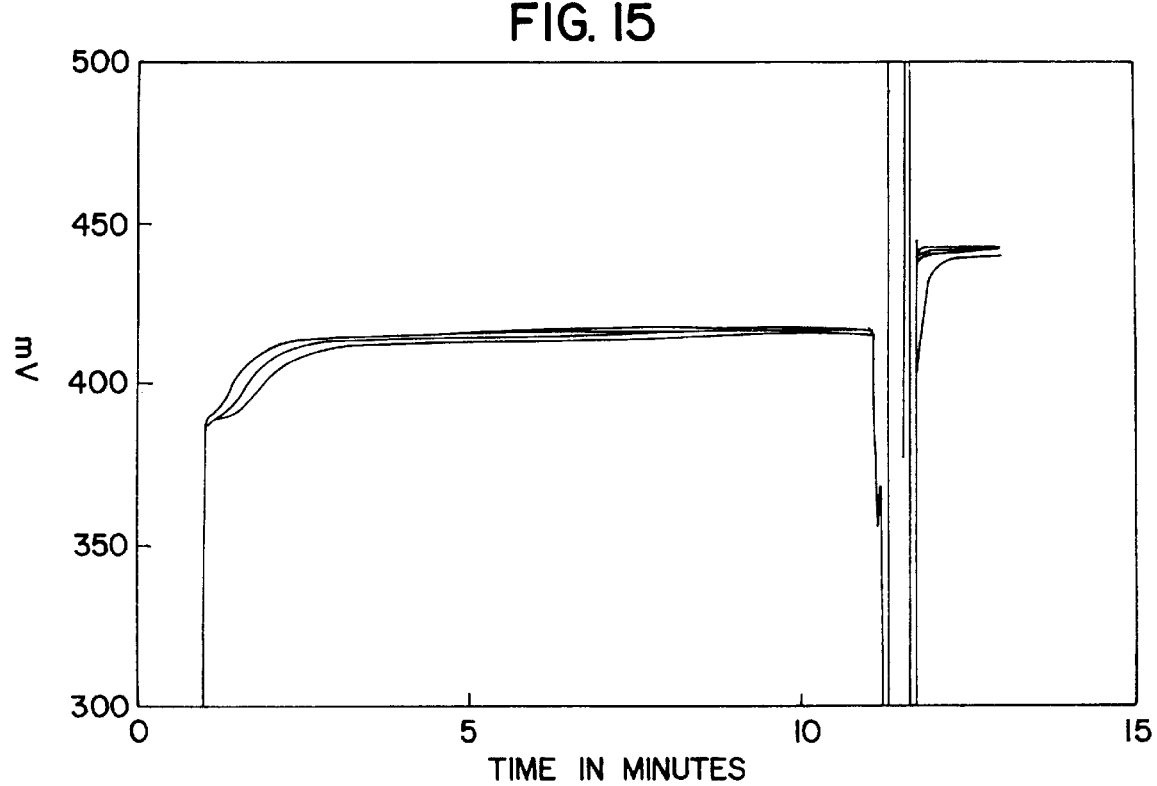
FIG. 15 is a graph showing wet up results for chip 3-62-1 in response to calcium.

Table 6 and FIG. 15 summarize the data for calcium (Ca) sensors without fortiophore (MTCE), with fortiophore (MTCE), and with fortiophore (MTCE) and silver salt. The results show that both MTCE and Ag salt are necessary to achieve the desired results. In this case sensors with fortiophore only respond slowly. At 60 seconds the offset potentials are not reproducible, but by ten minutes the offset potentials become reproducible (sd=2.1). The slope of sensors without fortiophore and sensors with fortiophore only are low due to their slow response. When Ag is added to the membrane, the response is fast, and reproducible. It is noted that other Ag salts have been used successfully with the calcium sensor.

Figure 16:
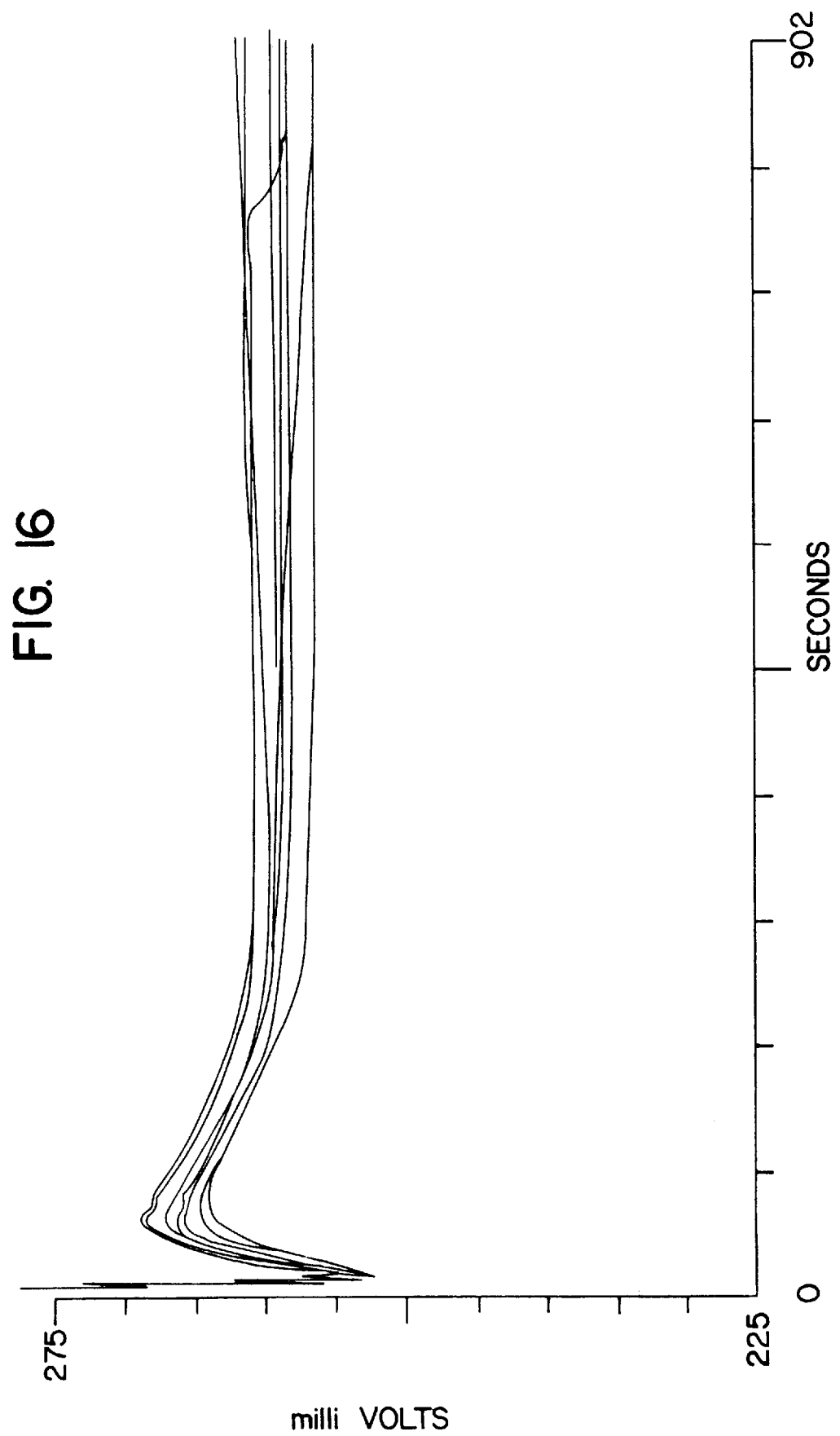
FIG. 16 is a graph showing wet up results for chip 30050-1 for pH measurement.

Table 7 and FIG. 16 summarize the data for pH sensors without fortiophore (MTCE), with fortiophore (MTCE) and with fortiophore (MTCE) and $AgNO_3$. The results show, as above, that both MTCE and Ag salt are necessary to achieve the desired results. Other Ag salts have been used successfully with this pH sensor.

Figure 17:
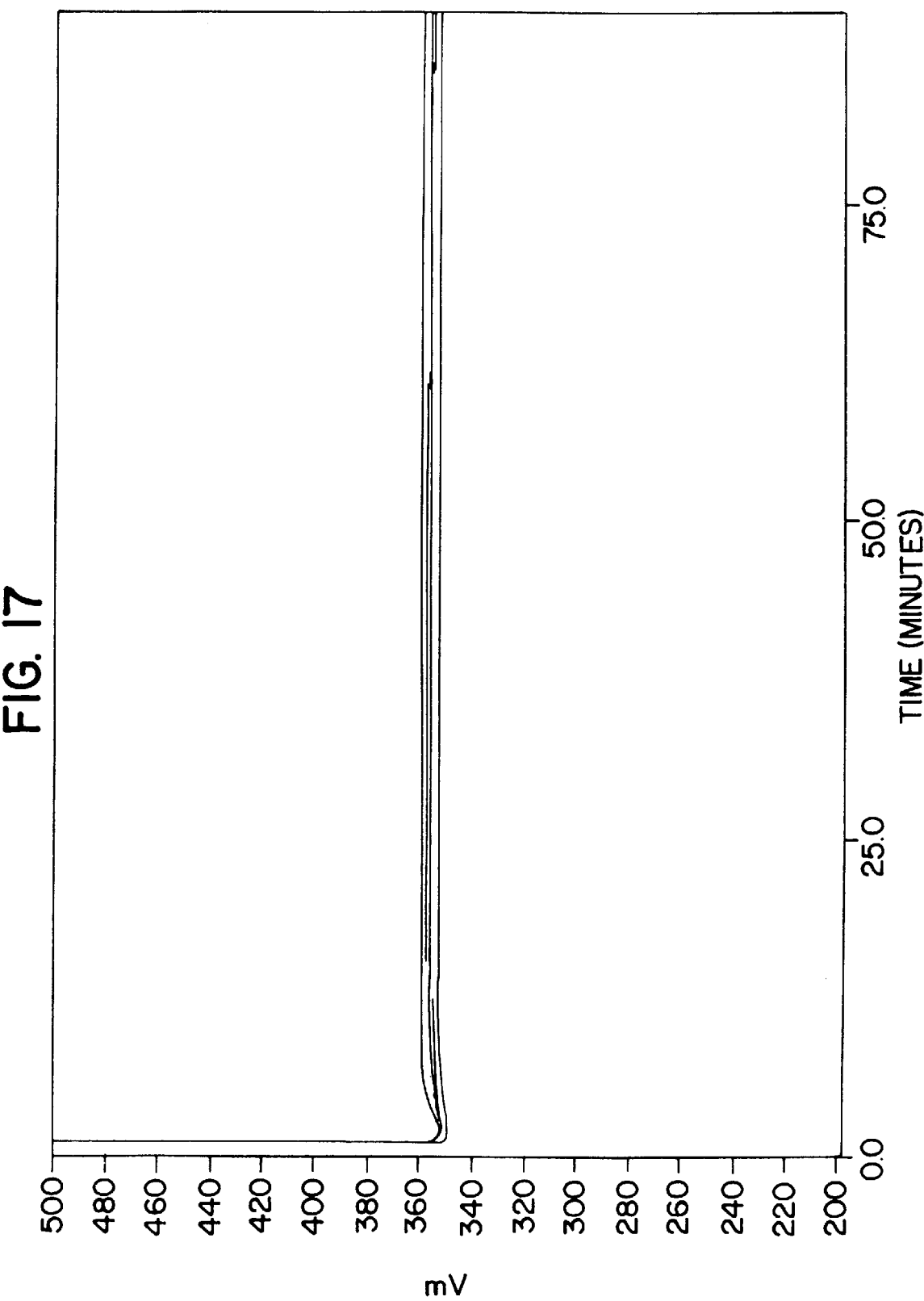
FIG. 17 is a graph of wet up results for chip 5-15-2 for sodium measurement.
Figure 18:
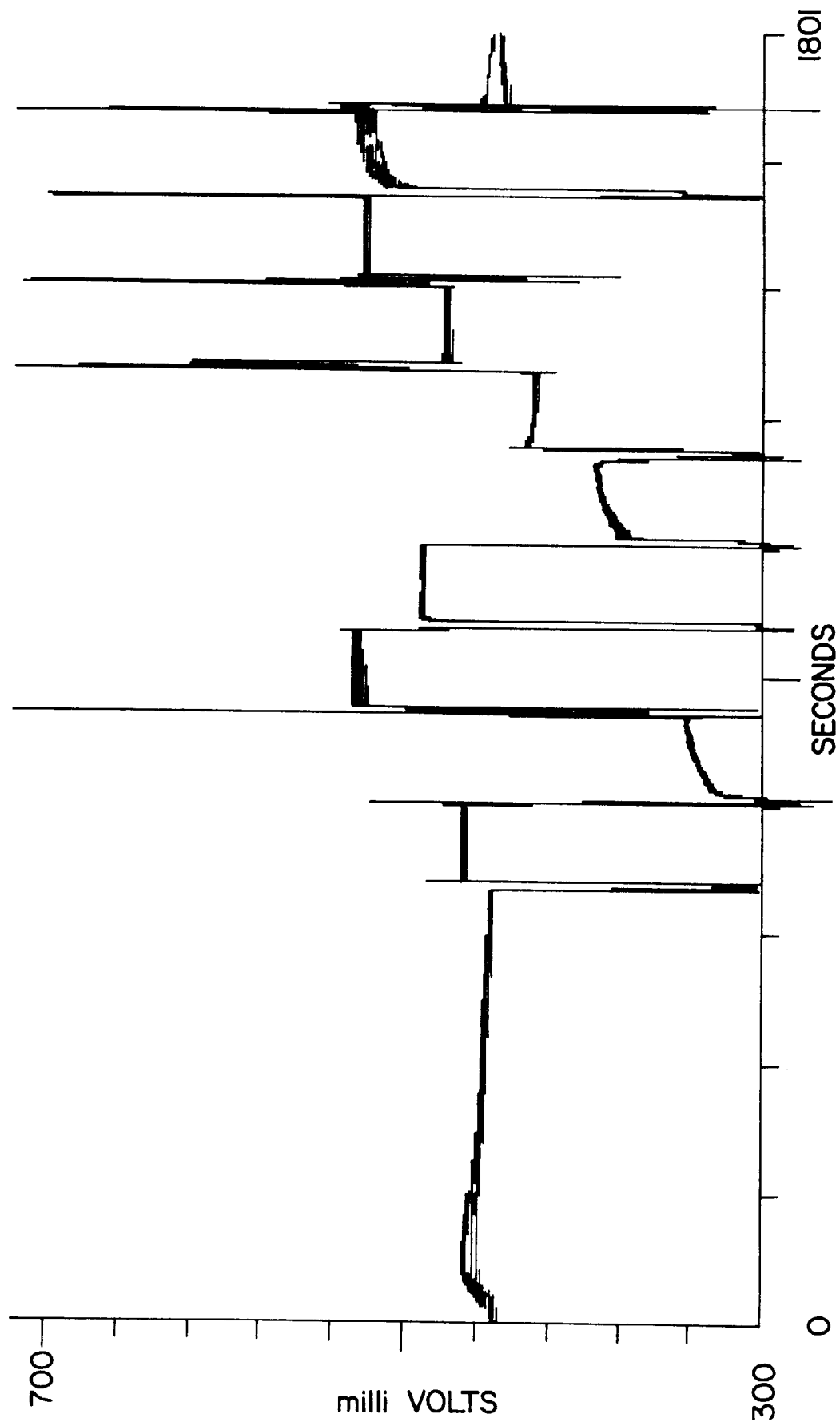
FIG. 18 is a graph showing wet up results for chip 129-32-1 for potassium measurement.
Figure 19:
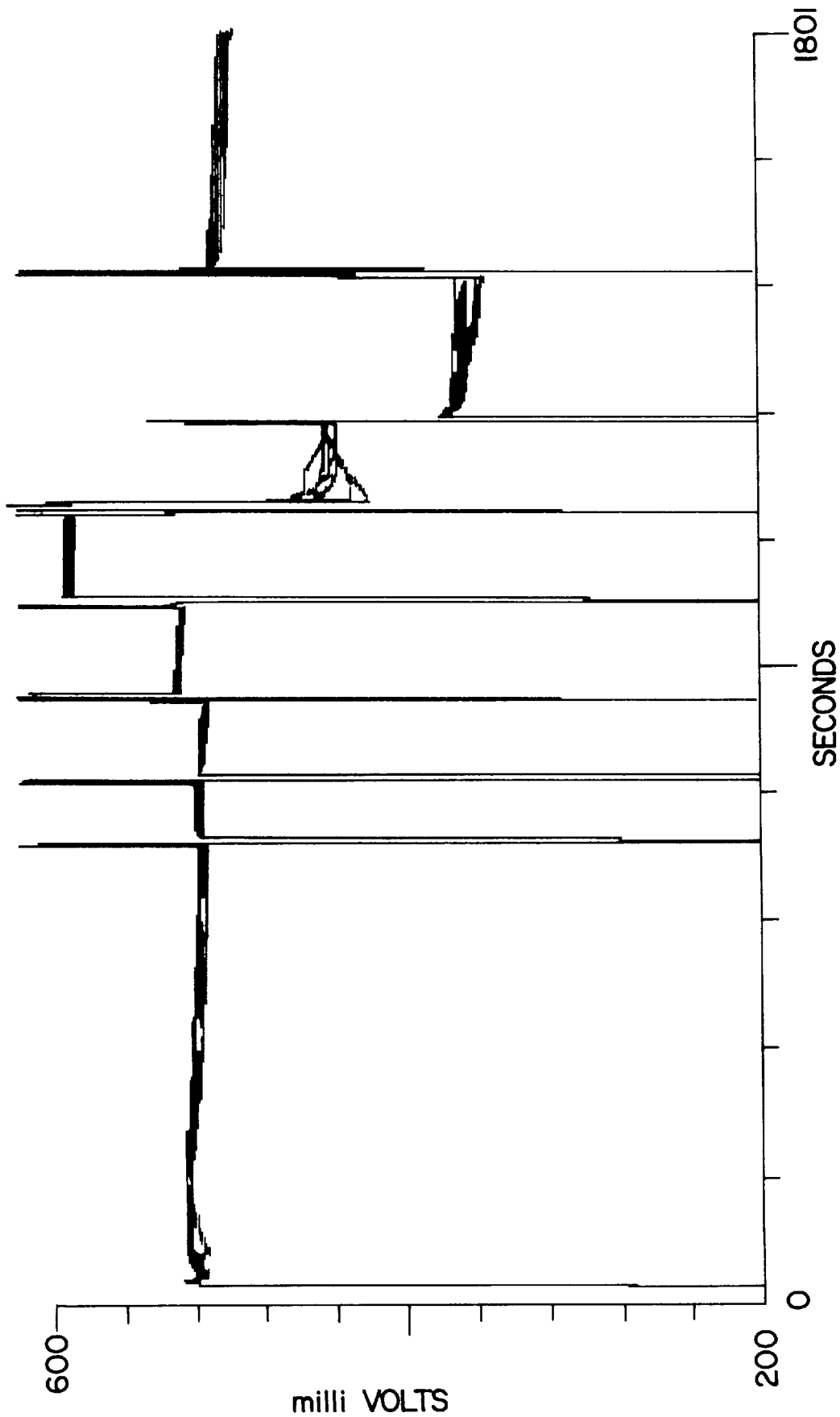
FIG. 19 is a graph showing wet up results for chip 53-17-1 for potassium measurement.

Table 8 and FIG. 17 summarize the data for sodium (Na) sensors, without fortiophore (MTCE), and with fortiophore (MTCE) and $AgNO_3$. The results show the same as above, that MTCE and Ag are necessary membrane components to achieve the desired results. Other Ag salts (AgTpClPB), plasticizers (TOTM) and ionophores (ETH 2120, and methyl monensin) have been used with similar results.

Table 9 and FIGS. 17–20 summarize potassium sensor data where AgBENZ is varied for wet up studies.

The invention described herein has industrial utility in the determination of ion content or other constitutents of test samples as will be evident to those skilled in the art. It is particularly useful for determination of the ion activity of biological test samples; yet can be used in similar devices determinations of other test samples of various sources.

It is to be understood that various other modifications will be apparent to and can readily be made by those skilled in the art, given the disclosure herein, without departing from the scope and material spirit of this invention.

TABLE 1

MEMBRANE COMPOSITION

| Chip | Composition (wgt. %) | Membrane Cast On |
|---|---|---|
| 2-6-1 | MTCE 0.4%, VAL 1.0%, DOP 68.6%, PVC 30% | Blank Ag |
| 2-19-1 | VAL 1.0%, DOP 68.0%, PVC 31% | Blank Ag |
| 2-6-7 | MTCE 0.4%, VAL 1%, DOP 68.2%, PVC 30%, KTPB 0.3% | Ag/AgCl |
| 2-19-4 | VAL 1.0%, DOP 68.1%, PVC 30.6%, KTPB 0.3% | Ag/AgCl |
| 2-39-10 | VAL 1.0%, PVC 30.9%, TOTM 68.1% | Blank Ag |
| 2-180-3 | VAL 10%, PVC 30.9%, TOTM 68.3%, MTCE 0.37%, $AgNO_3$ 0.25%, $KNO_3$ 0.04% | |
| 2-53-10 | MTCE 0.5%, VAL 1.0%, PVC 30.8%, TOTM 67.6% | Blank. Ag |
| 2-53-9 | UDCM 1.3%, VAL 1.0%, PVC 30.5%, TOTM 67.2% | Blank Ag |
| 3-62-1 | MTCE 0.4%, KTpClPB 0.5%, ETH1001 1.0%, PVC 30.0% TOTM 68.1% | Ag/AgCl |
| 30050-1 | MTCE 0.8%, TDDA 1.0%, $AgNO_3$ 0.6%, TOTM 64.4%, PVC 33.2%, kTpClPB 0.5% | Blank Ag |
| 5-15-2 | SHONO 1.0%, BHTCH 69%, PVC 30.0% | Blank Ag |
| 129-32-1 | MTCE 0.4% VAL 1.1% PVC 29.7% DUP 68.8% | Blank Ag |
| 53-17-1 | MTCE 0.4% VAL 0.9% AgBENZ 0.8% PVC 30.5% DUP 67.4% | Blank Ag |
| 129-34-6 | MTCE 0.4% VAL 1.1% PVC 29.7% DUP 68.8% | Ag/AgBENZ |

TABLE 2

STANDARD DEVIATION OF OFFSET POTENTIALS FOUR
ELECTRODES ON A CHIP (in mV)

| Membrane* | Ag | AgCl |
|---|---|---|
| MTCE 0.4% | 1.96 | 33.9 Avg. of two |
| MTCE 0.4% + KTPB (0.3%) | 2.97 | 4.45 2 chips |
|  | 4.41 | 7.26 Avg. one |
| KTPB (0.3%) | 7.80 | 9.13 chip |

*Each Membrane further comprising
VAL—1%
DOP—68%
PVC—30%

TABLE 3

SELECTIVITIES AND SLOPES

| | log k (potassium/M) | | |
|---|---|---|---|
| M | 2-6-1 | 2-6-7 | Target Value |
| Na+ | −3.6 | −3.2 | −3.6 |
| Ca++ | −3.7 | −3.7 | −2.9 |
| H+ | −3.4 | −3.4 | +2.8 |
| Slope (mV/dec) | 57.8* | 57.3** | 59.2 |

*corrected for junction potential: 59.4
**corrected for junction potential: 58.9

TABLE 4

PRECISION (SD in mV)

| | Reading Taken After (sec) | | | |
|---|---|---|---|---|
| | 10 | 30 | 44 | 90 |
| emf vs ext. ref electrode | | | | |
| -w/in electrode | | | | |
| -w/in same solution | | | | |
| 2-6-1 | 1.76 | 1.84 | 1.81 | 1.67 |
| 2-6-7 | 6.55 | 4.01 | 3.10 | 1.72 |
| differential emf | | | | |
| -w/in a pair of electrodes | | | | |
| -w/in same solution | | | | |
| 2-6-1 | 0.65 | 0.52 | 0.52 | 0.50 |
| 2-6-7 | 1.65 | 1.28 | 1.06 | 0.61 |
| across different solutions | | | | |
| 2-6-1 | 1.02 | 0.95 | 0.85 | 0.75 |
| 2-6-7 | 2.64 | 1.68 | 1.29 | 0.74 |
| target value | | | 0.53 | |

TABLE 5

SUMMARY OF POTASSIUM DATA WITH
VARIOUS FORTIOPHORES

| | NONE | MTCE | UDCN | DTCE |
|---|---|---|---|---|
| FORTIOPHORES | | | | |
| 60 sec data | | | | |
| OFFSET POTENTIAL (mV) | 365.0 | 565.0 | 724.0 | 766.5 |
| SD | 55.6 | 1.8 | 2.3 | 2.9 |
| DRIFT (mV/min) | 6.0 | 1.4 | −36.6 | −54.9 |
| SD | 4.0 | 0.6 | 12.7 | 12.1 |
| 60 min data | | | | |
| OFFSET POTENTIAL (mV) | 365.5 | 565.7 | 721.6 | 740.2 |
| SD | 68.7 | 3.2 | 2.4 | 3.9 |

TABLE 5-continued

SUMMARY OF POTASSIUM DATA WITH
VARIOUS FORTIOPHORES

| | NONE | MTCE | UDCN | DTCE |
|---|---|---|---|---|
| DRIFT (mV/min) | −0.2 | −0.3 | −0.2 | −0.1 |
| SD | 0.2 | 0.2 | 0.04 | 0.08 |
| MEMBRANE COMPOSITIONS | | | | |
| Val | 1.0% | 1.0% | 1.0% | 1.0% |
| UDCN | — | — | 1.3% | — |
| DTCE | — | — | — | 0.6% |
| MTCE | — | 0.4% | — | — |
| TOTM | 68.1% | 68.3% | 67.2% | 67.6% |
| PVC | 30.9% | 30.0% | 30.5% | 30.8% |
| AgNO₃ | — | 0.3% | * | * |
| KNO₃ | — | 0.08% | — | — |

*membranes had an uncontrolled amount of AgNO₃.

TABLE 6

SUMMARY OF CALCIUM SENSOR DATA

| | NO MTCE | MTCE | MTCE + Ag salt |
|---|---|---|---|
| 60 sec data | | | |
| OFFSET POTENTIAL (mV) | 358.0 | 297.3 | 413.3 |
| SD | 14.7 | 18.3 | 3.8 |
| DRIFT (mV/min) | 30.6 | 35.9 | 7.5 |
| SD | 8.1 | 10.7 | 3.5 |
| 10 min data | | | |
| OFFSET POTENTIAL (mV) | 375.2 | 327.6 | 414.6 |
| SD | 7.2 | 2.1 | 3.0 |
| DRIFT (mV/min) | −0.7 | −0.2 | −0.5 |
| SD | 0.6 | 0.5 | 0.5 |
| MEMBRANE COMPOSITIONS | | | |
| ETH1001 | 1.0% | 1.0% | 1.0% |
| MTCE | — | 0.6% | 0.6% |
| TOTM | 68.4% | 68.0% | 68.0% |
| PVC | 30.1% | 29.9% | 29.9% |
| KTpClPB | 0.5% | 0.5% | 0.5% |
| AgNO₃ | — | — | 0.001% |

TABLE 7

SUMMARY OF pH SENSOR DATA

| | NO MTCE | MTCE | MTCE + Ag salt |
|---|---|---|---|
| 60 sec data | | | |
| OFFSET POTENTIAL (mV) | 190.4 | 165.6 | 264.0 |
| SD | 11.4 | 15.6 | 1.6 |
| DRIFT (mV/min) | 27.5 | 16.1 | 1.7 |
| SD | 6.0 | 9.9 | 1.5 |
| 10 min data | | | |
| OFFSET POTENTIAL (mV) | 195.9 | 159.7 | 258.6 |
| SD | 2.8 | 8.5 | 2.3 |
| DRIFT (mV/min) | −0.9 | −1.7 | 0.02 |
| SD | 0.4 | 0.8 | 0.2 |
| MEMBRANE COMPOSITIONS | | | |
| TDDA | 1.0% | 1.1% | 1.1% |
| MTCE | — | 0.9% | 0.8% |
| AgNO₃ | — | — | 0.01% |
| KTpClPB | 0.6% | 0.5% | 0.5% |
| TOTM | 65.7% | 64.8% | 64.7% |
| PVC | 32.7% | 32.7% | 32.9% |

TDDA = Tridodecyl amine

TABLE 8

SUMMARY OF SODIUM SENSOR DATA

|  | NO MTCE | MTCE + Ag salt |
|---|---|---|
| 60 sec data | | |
| OFFSET POTENTIAL (mV) | 147.5 | 350.6 |
| SD | 16.2 | 0.9 |
| DRIFT (mV/min) | -1.3 | 0.3 |
| SD | 17.6 | 0.7 |
| 10 min data | | |
| OFFSET POTENTIAL (mV) | 188.4. | 356.4 |
| SD | 3.1 | 2.3 |
| DRIFT (mV/min) | -1.5 | -0.03 |
| SD | 0.2 | 0.03 |
| MEMBRANE COMPOSITIONS | | |
| SHONO | 1.0% | 1.0% |
| MTCE | — | 0.6% |
| BHTCH | 69.0% | 68.0% |
| PVC | 30.0% | 29.6% |
| AgTpClPB | — | 0.8% |

TABLE 9

SUMMARY OF POTASSIUM SENSOR DATA

| Chip # | 129-34-6 MTCE | 129-32-1 MTCE + AgBENZ | 53-17-1 MTCE + AgBENZ |
|---|---|---|---|
| 10 min data | | | |
| OFFSET POTENTIAL (mV) | 136.9 | 452.6 | 515.2 |
| SD | 30.9 | 1.0 | 2.0 |
| DRIFT (mV/min) | 0.9 | -0.2 | -0.8 |
| SD | 3.5 | 0.1 | 0.1 |
| MEMBRANE COMPOSITIONS | | | |
| VAL | 1.1% | 1.1% | 0.9% |
| MTCE | 0.4% | 0.4% | 0.4% |
| DUP | 68.8% | 68.8% | 67.4% |
| PVC | 29.7% | 29.7% | 30.5% |
| AgBENZ | — | * | 0.8%** |

*AgBENZ plated onto Ag-electrode
**Calculated from amount of AgBENZ saturated solution of THF used to make up membrane casting solution

We claim:

1. A sensor for measuring an ion in a test sample comprising:
   a) an internal reference element providing a reference redox couple and comprising an electrically conductive material comprising a species of ion capable of being complexed; and
   b) a membrane, said membrane being disposed on said internal reference element in direct contact therewith, said membrane including: an ionophore and a fortiophore, wherein said fortiophore is a neutral complexing agent complexed with the ion of said electrically conductive material which ion forms a portion of said reference redox couple to provide a solid electrochemical internal contact at the interface between the internal reference element and the membrane; and wherein said fortiophore is not selective in complexing the ion of the test sample to be measured by said sensor and said ionophore is selective for said ion in said test sample.

2. A sensor as described in claim 1, wherein said sensor further comprises: an inert substrate, and wherein said internal reference element is disposed on said inert substrate.

3. A sensor as described in claim 1, wherein said ion being measured is a cation or anion.

4. A sensor as recited in claim 1, wherein said internal reference element includes: a metal; an alloy; or a mixture of one or more non-metal substances and a metal or alloy.

5. A sensor as recited in claim 4, wherein said metal is a noble metal.

6. A sensor as recited in claim 5, wherein said noble metal is silver.

7. A sensor as recited in claim 1, wherein said membrane further comprises: a support material including: a hydrophobic organic polymer; and a plasticizer.

8. A device as recited in claim 7, wherein said hydrophobic organic polymer includes: poly (vinylchloride).

9. A sensor as recited in claim 7, wherein said plasticizer includes: dioctyl phthalate; trioctyl trimellitate; tetra-n-hexyl-3,3,'4,4'-benzhydrotetracarboxylate; o-nitrophenyl octyl ether; or diundecyl phthalate.

10. A sensor as recited in claim 1, wherein said membrane further comprises: a salt of said species of ion.

11. A sensor as recited in claim 1, wherein said fortiophore includes: dodecyl-16-crown-5-ether;undecyl cyanide; or 1,10-Dithia-18-crown-6-ether.

12. A sensor as recited in claim 1, wherein said ionophore includes: valinomycin; (-)-(R,R)-N,N'-N,N'-4,5-tetraethyl-3,6-dioxaoctaine diamide; bis (12-crown-4) methyldodecyl malonate; triodecylamine; or N,N,N',N'-Tetracyclohexyl-1,2-phenylenedioxydiacetamide.

13. A sensor device for measuring an ion in a test sample comprising: an internal reference element providing a reference redox couple and comprising an electrically conductive material comprising a species of ion capable of being complexed; an ionophore; a fortiophore; and a plastic membrane, said membrane being disposed on said internal reference element without any interposed liquid fill and carrying said ionophore; wherein said fortiophore is a neutral complexing agent complexed with said ion of said electrically conductive material which ion forms a portion of said reference redox couple and provides a reversible electrochemical interface between said internal reference element and said membrane; and wherein said fortiophore is not selective in complexing said ion in the test sample to be measured and said ionophore is selective for said ion in said test sample.

14. A sensor as recited in claim 13, wherein said membrane further includes a support material including: a hydrophobic organic polymer; and a plasticizer.

15. A sensor as recited in claim 14, wherein said hydrophobic organic polymer includes: poly (vinylchloride).

16. A sensor as recited in claim 14, wherein said plasticizer includes: diundecyl phthalate; dioctyl phthalate; trioctyl trimellitate;tetra-n-hexyl-3,3'4,4'-benzhydrotetracarboxylate; or o-nitrophenyl octyl ether.

17. A sensor as recited in claim 13, wherein said sensor further comprises: a salt of said species of ion, said salt being disposed on said internal reference element.

18. A device as recited in claim 13, wherein said fortiophore includes: dodecyl-16-crown-5-ether: undecyl cyanide; or 1,10-Dithia-18-crown-6-ether.

19. A device as recited in claim 18, wherein said ionophore includes: valinomycin; (-)-(R,R)-N,N'-N,N-4,5-tetramethyl-3,6-dioxaoctane diamide; bis (12-crown-4) methyldodecyl malonate; tridodecylamine; or N,N,N',N'-Tetracyclohexyl-1,2-phenylenedioxydiacetamide.

20. A device as recited in claim 13 wherein said ionophore is dispersed in said membrane.

* * * * *